(12) United States Patent
Pribenszky et al.

(10) Patent No.: US 7,879,539 B2
(45) Date of Patent: Feb. 1, 2011

(54) IMPROVING THE POST-THAW SURVIVAL OF MAMMALIAN BLASTOCYT OR SPERM BY APPLYING HYDROSTATIC PRESSURE PRIOR TO CRYOPRESERVATION

(75) Inventors: Csaba Pribenszky, Székesfehérvár (HU); Miklós Molnár, Budapest (HU)

(73) Assignee: Cryo-Innovation Kft., Szeged (HU)

( * ) Notice: Subject to any disclaimer, the term of this patent is extended or adjusted under 35 U.S.C. 154(b) by 1048 days.

(21) Appl. No.: 10/571,236

(22) PCT Filed: Sep. 8, 2004

(86) PCT No.: PCT/IB2004/051711
§ 371 (c)(1), (2), (4) Date: Dec. 15, 2006

(87) PCT Pub. No.: WO2005/022996
PCT Pub. Date: Mar. 17, 2005

(65) Prior Publication Data
US 2007/0087321 A1    Apr. 19, 2007

(30) Foreign Application Priority Data
Sep. 9, 2003 (HU) .................................. 0302888
Dec. 31, 2003 (HU) .................................. 0304124

(51) Int. Cl.
*A01N 1/00* (2006.01)
(52) U.S. Cl. ........................................................ 435/1.3
(58) Field of Classification Search .................. None
See application file for complete search history.

(56) References Cited

PUBLICATIONS

Arii et al., "Cryoprotection of Medaka embryos during development", Zoological Science 4 (5) : 813-818 (1987).*
Watson P.F. The effect of cold shock on sperm cel membranes. In: Morris, G.J. and Clarde, A. eds. Effects of low temperature on biological membranes. London: Academic Press; 1981. p. 189-218.*
Abe, F., and Horikoshi, K. (1995). *Hydrostatic Pressure Promotes the Acidification of Vasuoloes in Saccharomyces cerevisiae*. FEMS Microbiol Lett 130, 307-312.
Abe, F., and Horikoshi, K. (1997). *Vacuolar acidification in Saccharomyces cervisiae induced by elevations hydrostatic pressure is transient and is medicated by vacuoloar H+-ATPase*. Extremophiles 1, 89-93.
Abe, F., and Horikoshi, K. (1998). *Anyalysis of Intracellular pH in the Yeast Saccharomyces cerevisiae Under Elevation Hydrostatic Pressure: A Study in Baro-Physiology*. Extremophiles. 2, 223-228.
Abe, F., Kato, C. and Horikoshi, K. (1999). *Pressure-regulation metabolism in microorganisms*. Trends Microbiol 7, 447-453.
Aldridge, RE., Bruner, L.J. (1985). *Pressure ejects on mechanisms of charge transport across bilayer membranes*. Biochim Biophys Acta 817,343-354.
Archer, J., Gook, D.A., Edgar, D.H. (2003). *Blastocyst formation and cell numbers in human frozen-thawed embryos following extended culture*. Human Reproduction (Oxford, England) 18, 1669-1673.

Baguisi, A, Arav, A, Crosby, T.F., Roche, J.F., and Boland, M.P. (1997). *Hypothermic storage of sheep embryos with antifreeze proteins: development in vitro and in vivo*. Theriogenology 48, 1017-1024.
Bridgman P.W. (1911). *Water in the liquid and five solid forms under pressure*. Proceedings of the American Academy of Arts and Science 47,441-558.
Butz P, Ludwig H. (1986). *Pressure inactivation of microorganisms at moderate temperatures*. Physica B+C 139-140,875-877.
Fahy, G.M., MacFarane, D.R., Angell, C.A. and Meryman, H.T. (1984). *Vitrification as an approach to cryopreservation*. Cryobiology 21. 407-426.
Fukuda, A., Osawa, T., Oda, H., Tanaka, T., Toyokuni, S. and Uchida, K. *Oxidative stress response in iron induced acute nephrotoxicity: enhanced expression of heat shock protein 90*. Biochem Biophys Res Commun 1996; 219:76-81.
Garcia-Gardena, G. Fan, R., Shah, V., Sorrentino, R., Cirino, G., Papapetropoulos. *Dynamic activation of endothelialnitric oxide synthase by HSP90*. Nature 1998; 392: 821-4.
Graumann, P.L., Marahiel M.A. (1999). *Cold shock proteins CspB and CspC are major stationary-phase-induced proteins in Bacillus subtilis*. Arch Microbiol 171, 135-138.
Gross, M., Jaenicke, R. (1994). *Proteins under pressure. The influence of high hydrostatic pressure on structure, function and assembly of proteins and protein complexes*. Eur J Biochem 221,617-630.
Huang, S.Y, Kuo, Yh., Lee, W.C., Tsou, H.L., Lee, Yp., Chang, H.L. et al. *Substantial decrease of heat-shock protein 90 precedes the decline of sperm motility during cooling of boar spermatozoa*. Theriogenology 1999; 51:1007-16.
Huang, S.Y, Kuo, Y.H., Tsou, H.L., Lee, W.C.,King, Y.T., Huang, H.C. et al. *The decline of porcine sperm motility by geldanamycin, a specific inhibitor of heat shock protein 90 (HSP90)*. Theriogenology 2000; 53: 1117-84.
Ishwar, A.K., Memon, M.A. (1996), *Embryo transfer in sheep and goats: a review*. Small Ruminant Research 19, 35-43.
Jaenicke, R. (1991). *Protein stability and molecular adaptation to extreme conditions*. Eur J Biochem 202, 715-728.
LaTena, A., Brandi, A., Falconi, M., Spurio, R., Pon, C.L., Gualerzi, C.O. (1991). *Identification of a cold-shock transcriptional enhancer of the Escherichia coli major cold shock gene encoding nucleotide protein H-NS*. Proc Natl Acad Sci USA 88, 10907-10911.
Leibo, S.P. and Songsasen, N. (2002). *Cryopreservation of garnets and embryos of nondomestic species*, Theriogenology 57. 303-326.

(Continued)

*Primary Examiner* — Sandra Saucier
(74) *Attorney, Agent, or Firm* — Hahn & Voight PLLC; Jason D. Voight

(57) ABSTRACT

The present invention relates to a method for improving post-thaw survival of cryopreserved biological material comprising applying hydrostatic pressure to said biological material; keeping the said biological material at the hydrostatic pressure for a predetermined time period; releasing the hydrostatic pressure; and freezing the said biological material using any protocol applicable thereto. The invention also relates to the use of a pressurizing device for the pretreatment of a biological material that is to be cryopreserved, as well as to a pressurizing device for the pretreatment of a biological material that is to be cryopreserved, said device comprising a pressure chamber for receiving biological material, means to produce said pressure, and means to maintain said pressure in said chamber.

18 Claims, 4 Drawing Sheets

OTHER PUBLICATIONS

Medeiros, C.M.O., Forell, F., Oliveira, A.T.D., and Rodrigues, J.L. (2002). *Current Status of Sperm Cryopreservation: Why Isn't It Better?* Theriogenology 57:327-344.

Murakami, T.H., Zimmerman, A.M. (1973). *DNA synthesis in Tetrahymena: a pressure study.* Cytobios 7, 171-181.

Nowshari, M.A., Brem, G. (1998). *Effect of cryoprotectants and their concentration on post-thaw survival and development of expanded mouse blastocysts frozen by a simple rapid freezing procedure.* Theriogenology 50, 1001-1013.

Palou, E., Lopez-Malo, A., Barbosa-Canovas, G.V., Welti-Chanes, I., and Swanson, B.G. (1997). *Kinetic analysis of Zygosaccharomyces bailii inactivation by high hydrostatic pressure.* Lebensm.-Wiss. U. Technol. 30, 703-708.

Pearl, L.H.and Prodromou, C. *Structure and in vivo function of Hsp 90.* Curro Opin Struct Biol 2000; 10:46-51.

Pequeux, A., and Gilles, R. (1978). *Effects of high hydrostatic pressures on the activity of the membrane A TPases of some organs implicated in hydro mineral regulation.* Comp Biochem Physiol B Biochem Mol Biol 59, 207-212.

Phadtare, S., Alasina, J., Inouye, M. (1999). *Cold-shock response and cold-shock proteins.* CUff Opin Microbiol 2, 175-180.

Prodromou, C., Roe, S.M., O'Brian, R., Ladbury, J.E., Piper, P.W. amd Pearl, L.H. *Identification and structural characterization of the ATP/ADP-binding site in the HSP90 molecular chaperone.* Cell 1997: 90:65-75.

Rall, W.F., and Fahy, G.M. (1985). *Ice-free cryopreservation of mouse embryos at -196° C by vitrification.* Nature 313, 573-575.

Reubinoff, B.E., Pera, M.F., Vajta, G., and Trounson, A.O. (2001). *Effective cryopreservation of human embryonic stem cells by the open pulled straw vitrification method.* Human Reproduction 16,2187-2194.

Routray, P., Suzuki, T., Striissmann, C.A. and Takai, R. (2002). *Factors affecting the uptake of DMSO by the eggs and embryos of medaka, Oryzias latipes.* Theriogenology 58. 1483-1496.

Schmid, G., Liidemann, H. D., and Jaenicke, R. (1975) *High pressure effects on the activity of glycolytic enzymes.* Biophys Chern 3, 90-98.

Schuster, B., Sleytr, D.B. (2002). *The effect of hydrostatic pressure on S-layer-supported lipid membranes.* Biochim Biophys Acta 1563,29-34.

Seki, K., Toyoshima, M. (1998). *Preserving tardigrades under pressure.* Nature 395, 853854.

Silva,J.L.,Foguel, D., Royer, C.A. (2001). *Pressure provides new insights into protein folding, dynamics and structure.* Trends Biochem Sci 26,612-618.

Spilimbergo, S., Elvassore, N., Bertucco, A. (2002). *Microbial inactivation by high-pressure.* The Journal of Super critical Fluids 22,55-63.

Stachecki, J.J., Cohen, J., Schimmel, T., Willadsen, S.M. (2002). *Fetal development of mouse oocytes and zygotes cryopreserved in a nonconventional freezing medium.* Cryobiology 44,5-13.

Takahashi, T., Kakita, A., Takahashi, K., Yokoyama, I., Sakamoto, I., Yamashina, S. (2001). *Preservation of rat livers by supercooling under high pressure.* Transplantation Proceedings 33, 916-919.

Tinneberg, H.-R., Roberts, T.K., Cheng, C.Y. Mrettler, L. (1980). *High hydrostatic pressure as an improvement for sperm cryopreservation.* Archives of Andrology 5, 42-43.

Tuboly, E., Lebovics, V.K., Gail, 6., Meszaros, L., Farkas, J. (2003). *Microbiological and lipid oxidation studies on mechanically deboned turkey meat treated by high hydrostatic pressure.* Journal of Food Engineering 56, 241-244.

Van Wagtendonk-De Leeuw, A.M., Den Daas, J.H., Kruip, T.A., Rall, W.F. (1995). *Comparison of the efficacy of conventional slow freezing and rapid cryopreservation methods for bovine embryos.* Cryobiology 32, 157-167.

Van Wagtendonk-De Leeuw, A.M., Den Haas, J.H.G., and Rall, W.F. 1997. *Field trial to compare pregnancy rates of bovine embryo cryopreservation methods: vitrification and one step dilution versus slow freezing and three-step dilution.* Theriogenology 48, 1071-1084.

Weber, G., Drickamer, H.G. (1983). *The effect of high pressure upon proteins and other biomolecules.* Q Rev Biophys 16,89-112.

Welch, T.J., Farewell, A., Neidhardt, F.C., Bartlett, D.H. (1993). *Stress response of Escherichia coli to elevated hydrostatic pressure.* J Bacteriol175, 7170-7177.

Wemekamp-Kamphuis, H.H., Karatzas, AX., Wouters, J.A., Abee, T. (2002). *Enhanced levels of cold shock proteins in Listeria monocytogenes LO28 upon exposure to low temperature and high hydrostatic pressure.* Appl Environ Microbiol 68, 456-63.

Wen-Lei Cao et al. *Cryopreservation-induced decrease in heat-shock protein 90 in human spermatozoa and its mechanism.* Asian J Androl2003; 5:43-46.

Wouters, J.A., Jeynov, B., Rombouts, F.M., de Vos, W.M., Kuipers, O.P., Abee, T. (1999). *Analysis of the role of 7 kDa cold-shock proteins of Lactobacillus lactis MG 1363 in cryoprotection.* Microbiology 145, 3185-3194.

Yager, P., Chang, E.L. (1983). *Destabilization of a lipid non-bilayer phase by high pressure.* Biochim Biophys Acta 731,491-494.

Yamanaka, K., Fang, L., Inouye, M. (1998). *The CspA family in Escherichia coli: multiple gene duplication for stress adaption.* Mol Microbiol27, 247-255.

\* cited by examiner

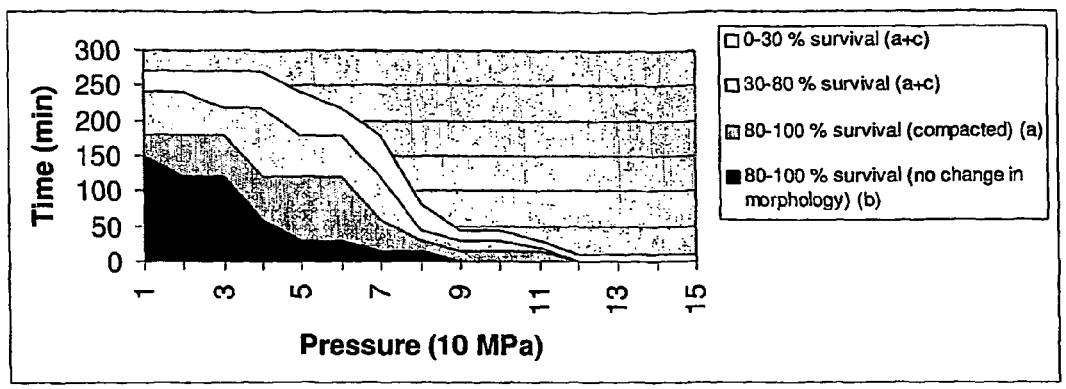
Figure 1.
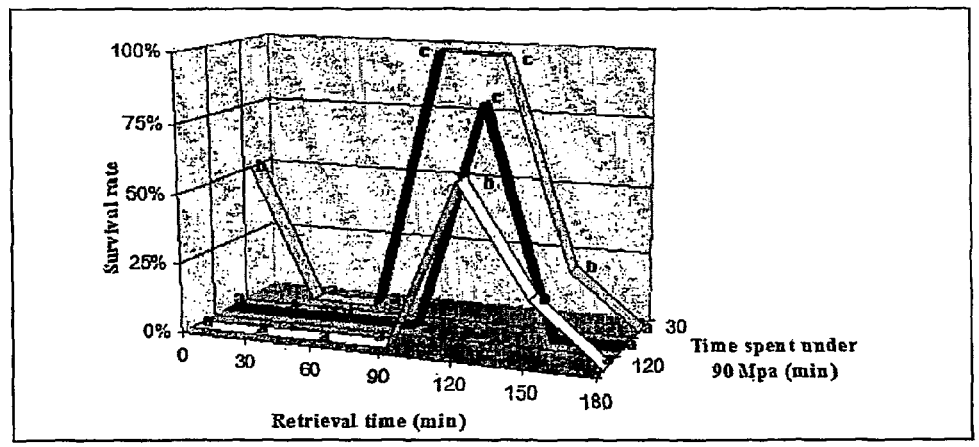
Figure 2.
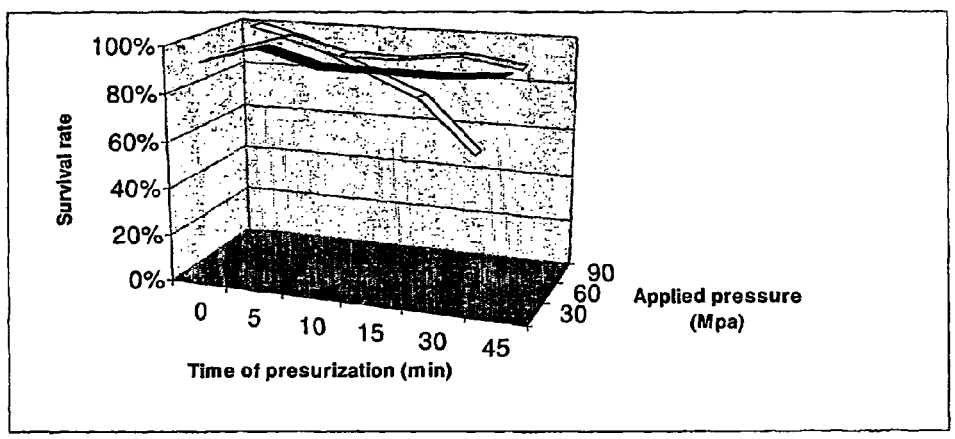
Figure 3.a

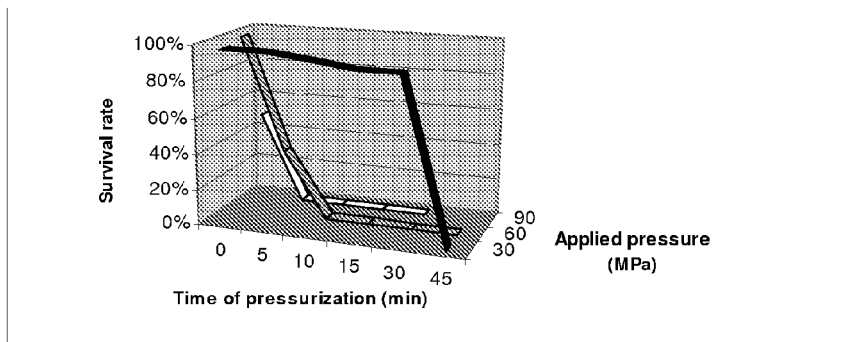
Figure 3.b
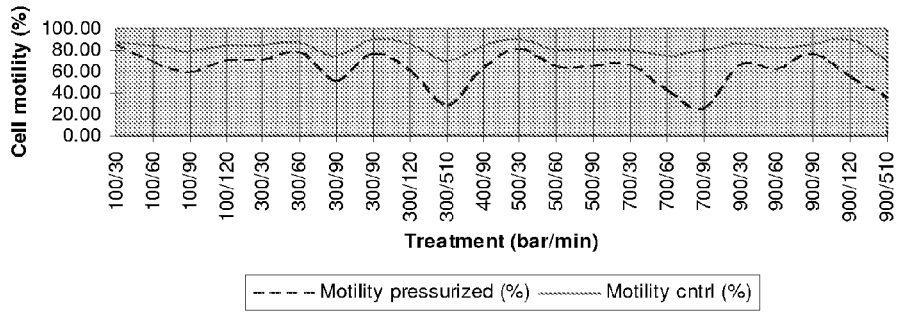
Figure 4
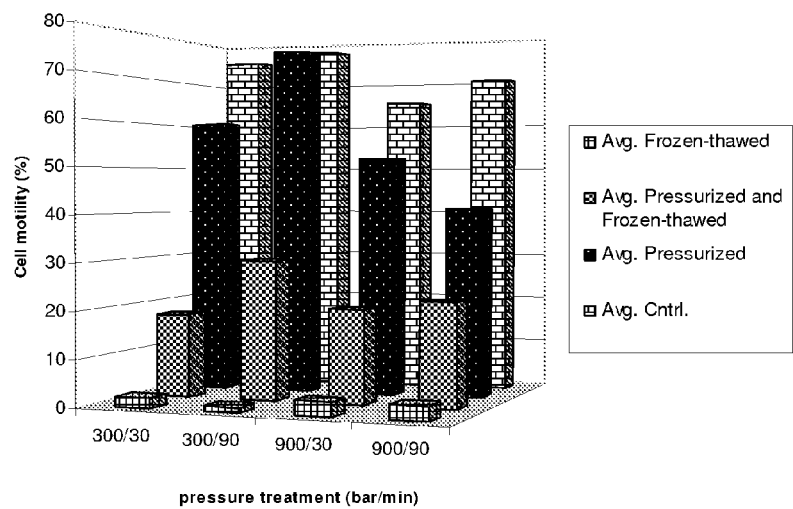
Figure 5

IMPROVING THE POST-THAW SURVIVAL OF MAMMALIAN BLASTOCYT OR SPERM BY APPLYING HYDROSTATIC PRESSURE PRIOR TO CRYOPRESERVATION

TECHNICAL FIELD

The present invention relates to a method for improving post-thaw survival of cryopreserved biological material comprising applying hydrostatic pressure to said biological material; keeping the said biological material at the hydrostatic pressure for a predetermined time period; releasing the hydrostatic pressure; and freezing the said biological material using any protocol applicable thereto. The invention also relates to the use of a pressurizing device for the pretreatment of a biological material that is to be cryopreserved, as well as to a pressurizing device for the pretreatment of a biological material that is to be cryopreserved, said device comprising a pressure chamber for receiving biological material, means to produce said pressure, and means to maintain said pressure in said chamber.

BACKGROUND ART

The process of cryopreservation is well established to store biological material for a wide variety of purposes in different fields of modern biology and biotechnology. These methods follow very similar basic steps:
1. Treatment of the biological material with a solution containing cryoprotective agent(s).
2. The next step comprises freezing of the biological material to subzero temperature.
3. The so prepared biological material is stored—even for very long time periods—at low temperature, for example in liquid nitrogen.
4. Prior to use the biological material is warmed back.
5. The cryoprotective agent(s) is (are) removed from the biological material. In addition, the biological material may require further steps to restore its original viability.

Several approaches has been tried to improve this above-outlined basic protocol, since the process of cryopreservation is harmful to biological material. Approaches to avoid ice formation through the ultra-rapid cooling and warming rates or by gradual depression of the equilibrium freezing point during cooling to −80° C. have not given a proper solution for every field of cryobiology. Attempts were made to improve survival after freezing: at vitrification highly concentrated aqueous solutions of cryoprotective agents supercool to very low temperatures, allowing intracellular vitrification (Rall and Fahy, 1985). Though Fahy et al. (1984) mentioned the possible use of considerably increased hydrostatic pressure as an additional factor that may facilitate vitrification, but also considered that it had few practical consequences in reproductive biology. Other studies report the use of antifreeze proteins (AFPs) which non-colligatively lower the freezing point of aqueous solutions, block membrane ion channels and thereby confer a degree of protection during cooling (Baguisi et al., 1987). The toxic effects of the cryoprotectants and the harmful consequences of the osmotic changes are not negligible at any of the described methods.

These procedures, at present, have a varying degree of efficiency for various applications. For example, in case of preserving embryos, the efficiency of cryopreservation ranges from 0 to 80 percent, depending on the species, freezing method, embryonic stage of development (Ishwar, 1996; Van Wagtendonk-De Leeuw, 1995, 1997; Medeiro, 2002; Reubinoff, 2001; Hammitta, 2003; Archer, 2003; Stachecki, 2002, Leibo and Songsasen, 2002). The success rates for the cryopreservation of human ova, being currently a popular issue, are also far from being satisfactory.

Since 1912 it has been known that water undergoes different phases when submitted to hydrostatic pressure at different temperatures (Bridgman, 1911) (FIG. 7). Solutions can be maintained unfrozen even at low subzero temperatures by applying a certain pressure to them (Bridgeman, 1970). High hydrostatic pressure (HHP) was previously used by Nakahashi et al. (2000, 2001) at subzero preservation of rat livers for transplantation in order to reduce cryoinjuries. This approach uses HHP to reduce substantially the freezing point of the culture medium, thus preserving the biological material at subzero temperature without any of the negative effects of cryopreservation. This approach was found unreliable by the present inventors in preserving mouse embryos, as outlined below in examples 2 and 3.

Hydrostatic pressure in the range of 30-50 MPa usually inhibits the growth of various organisms: the initiation of DNA replication is one of the most pressure-sensitive intracellular processes (Abe et al., 1999). The effects vary in severity depending upon the magnitude and duration of compression (Murakami and Zimmerman, 1973). The cell membrane is noted as a primary site of pressure damage (Palou et al., 1997). High hydrostatic pressure treatment can alter the membrane functionality such as active transport or passive permeability and therefore perturb the physico-chemical balance of the cell (Yager and Chang, 1983; Aldridge and Bruner, 1985; Macdonald, 1987; Schuster and Sleytr, 2002). A recent study by Routray et al. (2002) showed that hydrostatic pressure (5 MPa) facilitated the uptake of DMSO in the experiment conducted with eggs and embryos of medaka (*Oryzias latipes*), though there was a rapid loss in the viability. The physical or biochemical processes at altered pressure conditions are governed by the principle of Le Chatelier: all reactions that are accompanied by a volume decrease speed up considerably (Murakami and Zimmerman, 1973; Welch et al., 1993; Palou et al., 1997). The application of pressure can lead to a population of conformers of proteins, including partially or completely unfolded conformations. Pressure can cause the denaturation of proteins by the combined effects of breakage of intraprotein interactions and release of cavities followed by the binding of water (Schmid at al., 1975; Weber and Drickamer, 1983; Jaenicke, 1991; Gross and Jaenicke, 1994; Silva et al., 2001).

Recent reports state that hydrostatic pressure enhances the production of shock proteins (Welch et al., 1993; Wemekamp-Kamphuis et al., 2002). Studies describe that instabilities caused by sublethal cold shock in the normal protein synthesis in bacteria are overcome by the synthesis of so-called cold-shock proteins (CSPs, HSPs) (Phadtare et al., 1999). CSPs, HSPs are suspected to have many functions such as RNA chaperones (Graumann and Marahiel, 1999) or transcription activators (LaTena et al., 1991); it was assumed that they also play a role in the protection against freezing (Wouters et al., 1999). Further investigations found that the production of CSPs and HSPs are not only induced by cold shock, but by other environmental stresses also. In *E. coli*, for example, a type of CSP is produced by nutritional stress (Yamanaka et al., 1998). Another trial showed that high hydrostatic pressure treatment provoked the production of certain cold-induced proteins and heat shock proteins (Welch et al., 1993). Other recent reports state that hydrostatic pressure enhances the production of shock proteins (Wemekamp-Kamphuis, et al., 2002). Since cold-shock and high pressure-treatment both increases CSP and HSP levels, trials were conducted about the possibility of cross-protection.

Wemekamp-Kamphuis et al. (2002) found that the level of survival after pressurization of cold-shocked *Listeria monocytogenes* was 100-fold higher than that of the cells growing at 37° C.

While food-microbiologists study the above-mentioned processes in order to kill detrimental microorganisms (Butz and Ludwig, 1986; Wemekamp-Kamphuis et al., 2002; Spilimbergo et al., 2002), the aim of the present invention is to enhance the survival of cryopreserved biological material.

More attention is paid recently to study the role of shock proteins in cryopreservation. Huang et al. (1999) published that a substantial decrease of a shock protein, HSP90, might be associated with a decline in sperm motility during cooling of boar spermatozoa. Wen-Lei et al. (2003) reported that HSP90 in human spermatozoa was decreased substantially after cryopreservation that may result from protein degradation.

As a summary, HSP90, which is induced by high hydrostatic pressure is:

Cytosolic protein

Molecular chaperone, plays an essential role in stress tolerance, protein folding, signal transduction, etc.

Has been shown to possess an inherent ATPase that is essential for the activation of authentic client proteins in vivo (Pearland Prodromou, 2000).

Associated with semen motility:
  Activate nitric oxide synthetase (NOS) (Garcia-Gardena et al., 1998)
  Protect cells from reactive oxygen species (ROS) (Fukuda et al., 1996), which increase significantly during the cooling process and impair greatly sperm motility
  Involved in ATP metabolism (Prodromou et al., 1997). ATP level is diminished after cold shock, and would not restore later (Watson, 1981)

HSP 90 decreased substantially together with the decline of sperm motility after cooling boar semen. It was concluded, that HSP 90 might play a crucial role in regulating porcine sperm motility (Huang et al., 1999)

Geldanamycin, a specific HSP 90 inhibitor, significantly reduced the sperm motility of boar semen in a dose-and time dependant manner (Huang et al., 2000).

HSP90 decreased substantially after cryopreservation in human spermatozoa, together with the sperm motility; the decrease was not due to leaking, but a result of protein degradation (Wen-Lei CAO et al., 2003).

The accumulation of the pressure effects is lethal beyond a certain level: while irreversible changes of some biomolecules take place at higher pressures, at 300 MPa most bacteria and multicellular organisms die. Though tardigrades—in their active state they die between 100 to 200 MPa—can survive up to 600 MPa if they are in a dehydrated 'tun' state (Seki and Toyoshima, 1998).

The present inventors surprisingly found that by applying a hydrostatic pressure challenge, and then by following state of the art cryopreservation protocols, the survival of biological material can be improved significantly. In the context of the present invention, the term survival means, inter alia, improved continued in vitro and in vivo development, higher hatching or implantation and birth rates (in case of embryos); higher post thaw motility and/or improved capacity for fertilization (in case of sperm); improved continued in vitro and in vivo development, improved capacity for being fertilized, higher hatching or implantation and birth rates (in case of oocytes). It is appreciated that the term survival may encompass different other functional characteristics depending on the type of other biological material treated.

For this purpose the pressure tolerance of certain types of biological materials was established (see example 1, 5, and 6), followed by the investigation of several state of the art concepts to achieve the aim of improving the survival of pressurized biological material (see examples 2 and 3). Then the present inventors further investigated the effects of pressure treatment on different types of biological material and unexpectedly found the inventive method of pressure challenge to fulfill their objectives.

In this context we must emphasize that the present inventive concept equally applies to many different cryopreservation protocols, and the choice of those is not limited with respect to the invention. The only necessary step to include in the improved protocols is the step of hydrostatic pressure challenge; the parameters of which can be easily optimized by a person skilled in the art when following the teachings of the present description.

SUMMARY OF THE INVENTION

The present invention relates to a method for improving post-thaw survival of cryopreserved biological material comprising (a) applying hydrostatic pressure to said biological material, optionally according to a predetermined pressure-time profile;

(b) keeping the said biological material at the hydrostatic pressure for a predetermined time period;

(c) releasing the hydrostatic pressure;

(d) freezing the said biological material using any protocol applicable thereto.

In an embodiment, pressure used in the method according to the invention is in the range of 1 to 250 MPa. In preferred embodiments, the pressure is preferably in the range of 10 to 100 MPa, more preferably 20 to 75 MPa, and still more preferably 30 to 60 MPa.

In another embodiment, the hydrostatic pressure used in the method according to the invention is applied for a time period between 1 second and 300 minutes. In preferred embodiments, the pressure is applied preferably for a time period between 1 second and 150 minutes, more preferably between 1 second and 90 minutes, and still more preferably between 1 second and 60 minutes.

In other embodiments, the method according to the invention comprises the gradual release of the pressure over a time period between 1 second and 4 hours. In other embodiments the time period for releasing the pressure is between 10 second and 2 hours, or between 1 minute and 1 hour, or in other cases between 10 min and 30 min. The release of pressure can also be instantaneous.

In a preferred embodiment the method according to the invention is used in connection with biological material selected from the group consisting of oocytes, sperms, zygotes, morulas, blastocysts, embryos, stem cells, cells or tissues of a vertebrate animal.

Other preferred embodiments relate to a method wherein the said vertebrate animal is a fish, a bird or a mammal, preferably bovine, equine, caprine, ovine, swine, other livestocks, pets, primates, including human.

The present invention also relates to a pressurizing device for the pressure treatment of biological material, comprising:
  a pressure chamber for receiving biological material;
  means to produce pressure ranging from 1 to 250 MPa, preferably from 10 to 100 MPa, more preferably from 20 to 75 MPa, and still more preferably from 30 to 60 MPa; and means to maintain said pressure in said chamber for a time period between 1 second and 300 minutes, preferably between 1 second and 150 minutes, more preferably between 1 second and 90 minutes, and still more preferably between 1 second and 60 minutes.

In a preferred embodiment the present invention relates to a device wherein
said means for producing pressure is a piston and said pressure chamber is a cylindrical chamber receiving said piston;
high pressure sealing means are provided between the chamber and the piston and
manually and/or automatically operated means are provided for applying force on said piston.

In another preferred embodiment the present invention relates to a device, wherein said means for applying force on said piston is a plate like element having a surface abutting said piston, and there are means for adjusting the position of said piston within said chamber.

In other preferred embodiments the device comprises a system for controlling the depressurization of the pressure chamber over a time period between 1 second and 4 hours.

In other preferred embodiments the device further comprises a pressure gauge for indicating the pressure of the chamber.

In another preferred embodiment the said pressure chamber contains liquid medium.

In specific embodiments said pressure chamber has a wall of about 10 to 25 mm thickness, preferably of less than 20 mm thickness, said chamber having an inner diameter preferably less then 100 mm, more preferably less then 50 mm, particularly about 20 mm, and an inner height of preferably less then 250 mm, more preferably less then 100 mm, particularly about 200 mm.

In another preferred embodiment the invention relates to a device wherein the said biological material is selected from the group consisting of oocytes, sperms, zygotes, morulas, blastocysts, embryos, stem cells, cells or tissues of a vertebrate animal.

The present invention also relates to the use of a pressurizing device for the compression of biological material.

In a preferred embodiment the invention relates to a use of a pressurizing device wherein the pressurization is used as pretreatment for the cryopreservation of said biological material.

In preferred embodiments, the use of a pressurizing device may incorporate any of the cryopreservation procedures of the invention.

In preferred embodiments, the use of the invention involves a pressurizing device, which includes a pressure chamber suitable for receiving the biological material, and means to provide controlled pressure in the range of 1 to 250 MPa preferably 10 to 100 MPa, more preferably 20 to 75 MPa, and still more preferably 30 to 60 MPa.

In other preferred embodiments, the use of the invention involves a pressurizing device, which comprises means to maintain the said pressure for a time period between 1 second and 300 minutes, preferably between 1 second and 150 minutes, more preferably between 1 second and 90 minutes, and still more preferably between 1 second and 60 minutes.

In a preferred embodiment the use of the invention encompasses the use of a control system in connection with the pressurizing device for controlling the depressurization of the pressure chamber over a time period between 1 second and 4 hours.

In specific embodiments the invention also relates to a use of a pressurizing device wherein hydrostatic pressure is being achieved in the pressurizing device.

In another preferred embodiment the invention relates to the use of a pressurizing device, wherein the said biological material is selected from the group consisting of oocytes, sperms, zygotes, morulas, blastocysts, embryos, stem cells, cells or tissues of a vertebrate animal.

The invention further relates to the use of the pressurizing device according to the invention for the compression of biological material.

DETAILED DESCRIPTION

The present invention is described in more detail by using mouse embryos for the purpose of demonstrating the inventive concept. It should be apparent that the disclosed procedures equally apply to all kind of different biological materials which are routinely cryopreserved in the art. For the sake of easy access and manipulation, mouse embryos were selected as the subject of the detailed investigation. It is needless to say that the cryopreservation of embryos is in the forefront of the cryopreservation research due to its industrial and healthcare applicability. However, in the method according to the invention and similarly in the present description, the term 'mouse embryo' can be used interchangeably with the term 'biological material'. In the present specification, experimental data are also presented for bovine IVF embryos and bull sperm, providing unexpectedly enhanced post-thaw survival. Exemplary biological material can be, for example, pre- and postimplantation stages of embryos of different mammalian species, oocyte, sperm, stem cells, tissues, organs of vertebrate animals and human, or even the entire body. The vertebrate animal can be of any species, for example a fish, a bird or a mammal, preferably bovine, equine, caprine, ovine, swine, other livestocks, pets, primates, including human.

As highly developed eukaryotic organisms, mouse embryos are more susceptible to the effect of hydrostatic pressure than tardigrades and bacteria. The first objective therefore is to establish the basic features of mouse embryos under pressure concerning their morphology and survival.

For the thorough investigation of the method of the present invention, a prototype device was manufactured. The pressurizing device 1, depicted in FIG. 8, has been used to conduct the experiments discussed in the examples to follow.

The pressurizing device 1 comprises a cylindrical pressure chamber 2 having two openings 3, 4 one at the top and one at the bottom with a pressure gauge 5 being attached to the top opening 3 and a piston 6 being inserted through the bottom opening 4. The pressure gauge 5 might be any suitable gauge provided it is able to measure pressure in the region of interest, that is, in the range of 1 to 250 MPa, preferably 10 to 100 MPa, more preferably 20 to 75 MPa, and still more preferably 30 to 60 MPa. The pressure chamber 2 has an inside height of about 60 mm and a width of about 20 mm. The wall 7 of the chamber 2 is adapted to endure pressures up to 250 MPa, preferably at least up to 75 MPa, and still more preferably up to 60 MPa. The wall 7 of the chamber 2 is preferably made of a corrosion resistant material, which is preferably plastic or stainless steel. To enhance tight fitting between the inner side of the wall 7 at the bottom opening 4 and the piston 6, the latter is provided with a circumferential pressure sealing 8, such as for example a Teflon ring sealing. Such or other kind of pressure sealing 8 is preferably also used at the top opening 3 where the pressure gauge 5 is fitted. The part of the wall 7 surrounding the bottom opening has a peripheral protrusion forming a flange 9. The pressure chamber 2 is further equipped with a thick cap 10 for retaining and moving the piston 6 further inside the chamber 2. The cap 10 can be attached to the flange 9 by fixing means such as screws 11. The tensile strength of each screw must have an appropriately high value to resist the tensile forces due to the high pressure in the chamber 2. The pressure chamber 2 is filled with a medium 12 suitable for producing high pressure during comparatively small compression, which is established by forcing the piston further inside the pressure chamber 2. Such medium can be any known type of non-solid medium 12 (preferably fluid or gelatinous medium 12) applicable in the field of high-pressure technology, however, for the purpose of the investigation, ordinary water was used. To prevent heating of the medium 12 during compression the wall 7 of the pressure chamber 2 is preferably from a heat-conductive material.

It will be appreciated that the above-described pressurizing device 1 may be constructed with such diameters so as to offer portable means for implementing the improved cryopreservation method of the present invention. The following sizes serve only as an example and it is understood that a person skilled in the art can easily envision both larger and smaller embodiments. The pressure chamber 2 has an inner height $H_i$ of 60 mm and an inner diameter $D_i$ of 20 mm, which also corresponds to the diameter of the piston 6. The height $H_p$ of the piston 6 can be selected proportionally to $H_i$, for example in the short test device it was 20 mm. The wall 7 of the chamber 2 has a thickness $D_w$ of about 10 mm. The pressure sealing 8 around the piston 6 has a height $H_s$ of 5 mm and a thickness $D_s$ of 2 mm The screws 11 used for fixing the cap 10 to the flange 9 can have a diameter D of 8 mm. Commercially available screws 11 of this size can have a tensile strength of 800 MPa, which is sufficient for ensuring a pressure up to 200 MPa. The actual sizing of the device can be designed according to the biological material to be treated and the available means to apply the biological material into the device.

During the pretreatment of the mouse embryos to be cryopreserved, the embryos (preloaded into plastic straw with appropriate embryo holding solution) were placed inside the pressure chamber 2 into the fluid medium 12 (the later being ordinary water); the piston 6 was inserted in the bottom opening 4 without applying any extra force on it, and the cap 10 was attached to the flange 9 of the chamber 2 by means of the screws 11 in a position abutting the piston 6, which, in the uncompressed state of the medium 12, protrudes partly from the chamber 2. Following this, the cap was drawn nearer to the bottom opening 4 to force the piston 6 further inside the pressure chamber 2 by tightening the screws (either manually or by a screwing automatism) at a rate and to such extent as to achieve the required pressure conditions for the particular experiment being conducted. The resulting pressure inside the chamber 2 was monitored by the pressure gauge 5. After the desired period of time has elapsed the depressurizing of the chamber took place by either gradually loosening the screws 11 or by taking out the pressure gauge 5 from the top opening thereby letting the fluid medium 12 to expand in a quasi-instantaneous way.

The means for placing the embryos into the chamber is not limited to plastic straw. Depending the specific application and the biological material, the sample to be treated can be placed into different holding structures. For example, embryos or cells can be placed on cryoloops or electron microscopic grids. In a different embodiment, a drop of holding solution with the biological material may be simply covered with mineral oil as the fluid medium 12. In this case, the whole pressurizing device could be miniaturized, allowing it to fit under a stereomicroscope to enable easy recovery. In case of macroscopic biological material, there is no need for specific placing means, the sample can be placed into the chamber, and the fluid medium 12 itself can be the holding solution. Any means for placing and/or holding the biological material in the chamber that allows the effects of high hydrostatic pressure take place on the biological material, are within the scope of the invention.

The pressurizing device 1 can be fully automated by providing a programmable control system. Such control system may include the following as input parameters: pressure gain rate, desired time at maximum pressure and pressure release rate. Temperature control means may also be used, although having highly thermoconductive material as the wall 7 of the pressure chamber 2 might prove sufficient to prevent harmful temperature variations. The temperature control means can be envisioned to be as an integrated pressurizing-freezing device to provide a one-step solution for the cryopreservation process. In that scenario both the pressurizing and freezing components can be automated and fitted with means for programming the pressure treatment and freezing according to the requirements of different biological materials.

It is also envisioned a portable device which can be very similar to the above-described test unit and would provide easy and simple way for treating biological material, then this step could be followed by readily available technologies for preserving said biological material. Such approach would help practitioners in remote locations, or could be used in different projects, such as wild life conservation.

Carefully designed experiments were conducted to investigate the pressure tolerance of different biological materials. The choice of pressure and time scale used was defined to give the widest applicable range for later practical applications. For example, as shown in FIG. 7, the phase change temperature of water decreases with pressure from 0° C. at 0.1 MPa to −21° C. at 210 MPa and the opposite effect is observed above this pressure level. Therefore, the pressure for the use in the method according to invention is selected in the range from 1 MPa to 250 MPa, or even up to the point where the medium freezes at the operating temperature of the device. More particularly, the hydrostatic pressure that can be applied to the expanded blastocyst stage embryos is 1, 5, 10, 15, 20, 25, 30, 40, 50, 60, 70, 80, 90, 100, 110, 120, 130, 140, 150, 200 or 250 MPa, or any value in between these intermediate ranges.

The hydrostatic pressure can be applied to said biological material according to a predetermined pressure-time profile. It will be appreciated by the person skilled in the art that, depending on the biological material to be treated, the pressure applied to the material may be increased gradually over time. The profile appropriate for a given biological material can be determined empirically, and it may be linear, stepwise, or other conventionally used time profile.

Similarly, a wide period of time can be selected for the biological material to be kept under high hydrostatic pressure. More particularly, the mouse embryos are kept under the selected pressure for a time period between 1 second and 6 hours, more specifically 1 s, 5 s, 10 s, 20 s, 30 s, 40 s, 50 s, 1 min, 2 min, 3 min, 4 min, 5 min, 6 min, 8 min, 10 min, 15 min, 20 min, 30 min, 40 min, 50 min, 60 min, 70 min, 80 min, 90 min, 120 min, 150 min, 180 min, 210 min, 240 min, 300 min or 360 min. The time the embryos survive under pressure reduces with increasing pressure.

It is appreciated by the person skilled in the art that the time between the end of the pressure pre-treatment and the beginning of the cryopreservation can be considerably different in specific embodiments. Depending the given protocol, the state of the biological material may change in this time frame. This period may allow for the physical recovery of the cells if long enough or, conversely, cellular processes may commence, i.e. the synthesis and accumulation of shock proteins could take place. In different circumstances these effects may prove either beneficial or damaging; therefore optimization of the protocol may be necessary in this regard through experimentation.

FIG. 1 shows that embryos can survive a substantial amount of pressure without any visible change in their morphology (e.g., 90 MPa for 1 s or 30 MPa for 2 h). The embryos compacted depending on the magnitude and the duration of the applied pressure treatment. Without limiting the scope of the invention by theory, we assume that pressure can not be directly responsible for squeezing the water out of the blastocysts. Based on the cited documents, the compaction of the embryos was due to the consequences of pressure induced production of different proteins (cold-shock proteins, CSPs), reversible alterations in protein structure and metabolic processes. Compacted embryos could regain their normal morphology after 4-5 hours of in vitro culture, and resume development similarly to controls (e.g., embryos challenged by 90 MPa for 30 min or 30 MPa for 3h).

Without limiting the scope of the invention by theory, it can be postulated from the studies with IVF bovine embryos that compaction is not a criterion for the optimal pressure pretreatment. Compaction can be the result of pressure-altered membrane permeability, altered diffusion and active transport through the cell membranes. This reversible change in morphology can be considered as a morphological 'sign' which marks that the embryo was treated with a 'sub-lethal' impact. According to the literature, the 'sub-lethal' shock is an impact that induces the production so-called 'shock proteins', which are suspected to play role in the improvement of the success rate of cryopreservation.

However, in certain applications the compacted embryos can preferably be selected for cryopreservation. After pressurization, expanded blastocysts become compacted and stay in this form for 3-4 hours, then they re-expand. Based on this phenomenon, embryos treated with pressure before the freezing process can be selected. Since the morphological changes of the embryos and the beneficial effects of the pressure pretreatment may come from the altered protein structure and/or features and/or the enhanced production of different pressure-induced proteins, the examination of these proteins can be indicative of the high hydrostatic pressure applied to the biological material before the cryopreservation process.

The pressure pre-treatment also correlates to a certain degree with the time when embryos regain their normal development after cryopreservation. Observing this process can indicate the nature of a pre-treatment, as using high hydrostatic pressure can considerably shorten the time necessary for regeneration.

The higher the magnitude of the pressure, the less time the embryos survive. Pressure impact exceeding a certain magnitude and duration caused irreversible changes: embryos became disintegrated after 2 hours of in vitro culture or were already disintegrated after decompression (e.g., embryos challenged by 90 MPa for 2 h or 30 MPa for 5 h). The person skilled in the art should be capable of determine these limit-pressures and limit-times by routine experimentation with respect to the specific biological material used.

It will be appreciated that the survival rate of the pressurized embryos can be enhanced by gradual decompression thereof. Studies showed that the survival rate of the pressurized embryos increased strikingly if they were retrieved gradually. While 60 minutes at 90 MPa was lethal for all of the embryos, 80% survived when 120 min. gradual decompression was used. The decompression time is also a feature of the present invention which is up to the person skilled in the art to determine in view of the specific application. More particularly, the mouse embryos kept under the selected pressure are decompressed for a time period between 1 sec. and 4 hours, more specifically 1 s, 5 s, 10 s, 20 s, 30 s, 40 s, 50 s, 1 min, 2 min, 3 min, 4 min, 5 min, 6 min, 8 min, 10 min, 15 min, 20 min, 30 min, 40 min, 50 min, 60 min, 70 min, 80 min, 90 min, 120 min, 150 min, 180 min, 210 min or 240 min. Similarly to the application of the pressure, the decompression could be done according to a predetermined pressure-time profile.

Again, without being limited by theory, a possible explanation of this feature could be that a considerable amount of $CO_2$ is generated under pressure (Abe and Horikoshi 1995). The hydration and ionization of $CO_2$ ($HCO_3^-$ and $H^+$) are facilitated by elevated pressure because the reaction is accompanied by a decrease in volume (#0.26 ml/mol) in a manner dependent on the magnitude of the pressure applied (Palou at al. 1997, Welch at al. 1993). The intracellularly produced carbon dioxide instantly dissolves, and then dissociates to give $HCO_3^-$ and $H^+$, thus also reducing the intracellular pH (Abe and Horikoshi 1995, 1997, 1998, Abe et al. 1999). It can be assumed that the equilibrium maintained by elevated pressure is lethal for the embryos at atmospheric pressure. It may be also hypothesized that the instant decrease of pressure causes elevated release of $CO_2$ from its hydrated and ionized form from the cytoplasm, causing immediate death of the embryos. On condition of a certain decompression time, the plasma membrane proteins ($H^+$-ATPase) (Schmid et al. 1975, Péqueux and Gilles 1978) reversibly inactivated by elevated hydrostatic pressure, start to function again, (together with passive diffusion) shifting the equilibrium gradually towards the physiological state.

High hydrostatic pressure (HHP) was previously used by Nakahashi et al. (2000, 2001) at subzero preservation of rat livers for transplantation in order to reduce cryoinjuries. This approach uses HHP to reduce substantially the freezing point of the culture medium, thus preserving the biological material at subzero temperature without any of the negative effects of cryopreservation. To investigate this method of cryopreservation in the case of mouse embryos, studies were designed to pressurize embryos at 0° C. The survival of the embryos reduced significantly. While at room temperature (RT) embryos had an average survival rate of 90% at 30 MPa for 45 min, none of the embryos survived the same impact at 0° C. After 10 minutes or 5 minutes at 0° C., 0% of the embryos survived at 60 MPa and at 90 MPa, respectively. In contrast, at room temperature, the survival rate was around 90% in both cases. Embryos were also pressurized at 0° C. and were decompressed gradually. The application of gradual decompression at low temperature did not have a beneficial effect on the embryosurvival. Based on these findings, the use of the phenomena is not applicable in this form, since pressure and low temperature together proved to be lethal for the embryos.

The present invention relates to the improvement post-thaw survival of cryopreserved mouse blastocysts by hydrostatic pressure challenge. This can be evaluated by transferring the pressurized embryos, following their treatment by any type of cryopreservation protocol and thawing, to culture medium and/or into pseudopregnant recipients. In vitro development, implantation and further uterine development and birth of healthy pups are obvious proof of their biological and genetic potential.

As we disclosed in detail above, the survival rate of cryopreserved expanded mouse blastocysts could be improved by a certain pressure treatment before the freezing procedure. A pressure impact of 60 MPa for 30 min was applied to the blastocysts, where approximately 80% to 90% of the embryos became compacted and survival was not different from the untreated control. According to the results of the in vitro evaluation, the applied pressure treatment strikingly improves the in vitro development of the embryos after freezing. In vitro studies showed that the hydrostatic pressure challenge not only improves the survival rate of the blastocysts treated, but also improves the recovery time necessary to the embryos to regain their native state. In our exemplary studies, after 6 hours 98% of the pressure treated blastocysts were morphologically (diameter, structural integrity, and general morphology) exactly identical to the control embryos and 95% of the blastocysts fully hatched within 20 hours, together with the controls. Embryos frozen without pressure treatment reexpanded only 20 hours after thawing. The proportion of the re-expanded blastocysts was significantly inferior to those receiving pressure treatment (46% vs. 98%). In addition, no embryos hatched from this group. Therefore, it is clear that the method according to the invention is suitable to obtain highly viable mouse embryos.

DESCRIPTION OF DRAWINGS

FIG. 1 shows the survival rate of embryos at different pressures between 10 MPa and 150 MPa (by 10 MPa) for different times (1 s, 5 min, 15 min and 30 min to 300 min by 30 min intervals), at room temperature. 14-16 embryos were used in each group; each experiment was repeated 3 times. The survival rate of embryos in the fields marked with 'a' and 'b' is not different from the untreated control ($p<0.05$).

FIG. 2 shows Survival rates of embryos pressurized with 90 MPa for 30, 60, 120 min and decompressed for 30-180 min. (With instant decompression survival at 30, 60 and 120 min was 50%, 0%, 0%, respectively). Survival rates marked on the figure with different superscripts are significantly different from each other ($p<0.05$).

FIG. 3a shows the survival of embryos pressurized with 30, 60 and 90 MPa for 1 sec to 45 min, at room temperature.

FIG. 3b shows the survival of embryos pressurized with 30, 60 and 90 MPa for 1 sec to 45 min, at 0° C. 12-15 embryos were used in each of the groups; each experiment was repeated 3 times. Significant differences are seen between the groups pressurized at room temperature and at 0° C. ($p<0.01$).

FIG. 4 shows the average values of sperm motility (pressurized and control).

FIG. 5 shows the average motility of the sperm of Bull I after pressurization and freezing-thawing.

EXAMPLES

Figure 6:
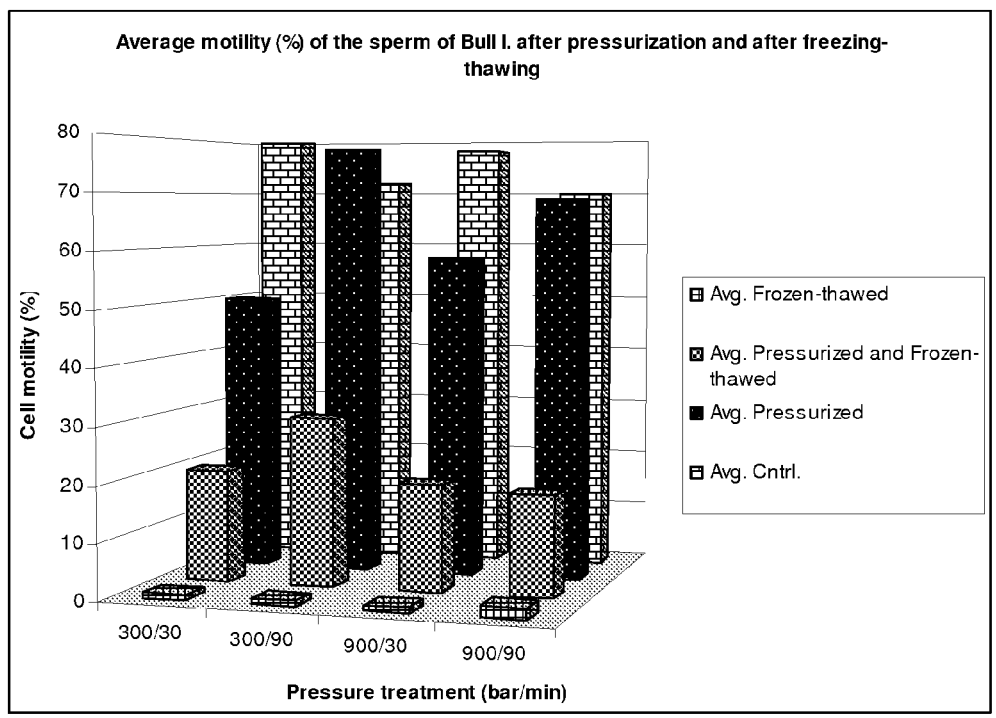
FIG. 6 shows the average motility of the sperm of Bull II after pressurization and freezing-thawing.
Figure 7:
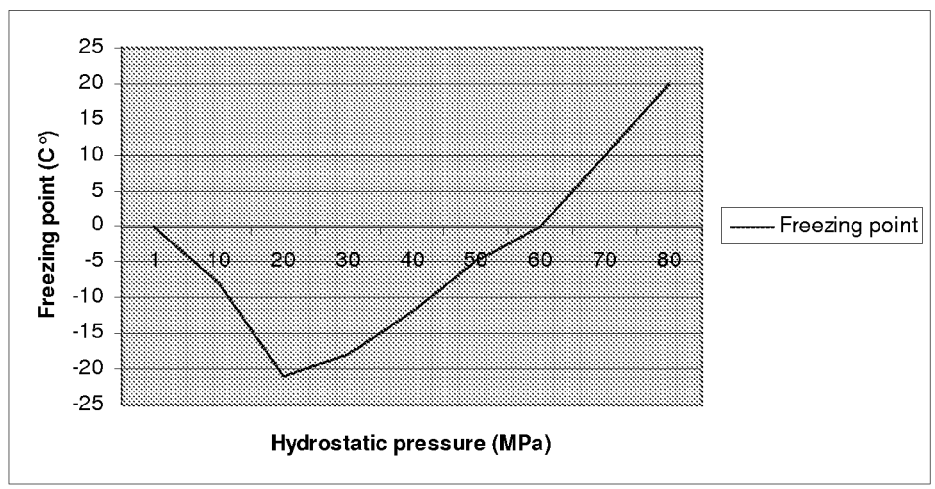
FIG. 7 shows the freezing point of water at different pressures.
Figure 8:
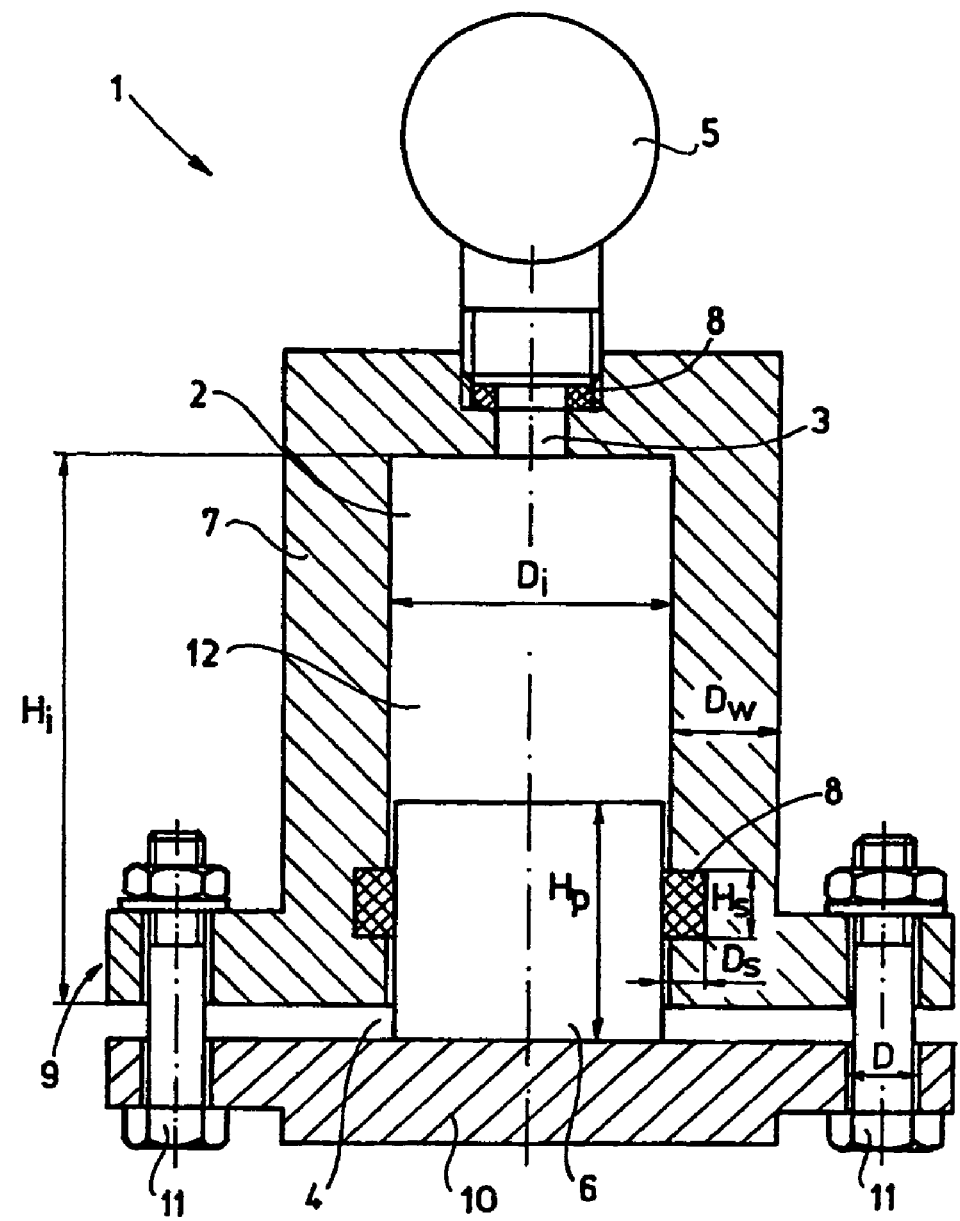
FIG. 8 is a schematic cross sectional view of a possible pressurizing device according to the present invention.

Materials and Methods for Example 1 to 4

Experimental Animals and Embryo Production

CB6F1 (Charles River, Germany) mice were housed under standard conditions (22+/−2° C.; 12 h dark/12 h light; water and food ad libitum).

Females were superovulated by intraperitoneal injection of 10 IU of PMSG (Sigma, USA) followed by 10 IU of hCG (Sigma, USA) 46 h later. After 6 hours of hCG administration, females were mated with fertile males in monogamous pairs. One to two cell stage embryos (Day 0 and Day 1) were harvested by flushing the oviduct with FertiCult Flushing medium (FertiPro N. V., Belgium). Embryos were cultured at 37° C. in thermostat with 5% $CO_2$ and maximal humidity in air. Embryos, between one-cell and compact morula stages, were cultured in G 1.2 medium (Vitrolife, Sweden) under mineral oil, Ovoil (Vitrolife, Sweden). Then, the embryos were transferred and cultured in G 2.2 (Vitrolife, Sweden) under Ovoil until the expanded blastocyst stage.

Pressurization

Blastocysts were loaded into plastic straws without air-bubbles (7-9 embryos/straw), with M2 (Sigma, USA), then straws were heat-sealed. Straws were placed into the pressure-chamber filled with water as pressure medium. The custom-made pressurizing device, which was capable of providing precisely controlled pressure in the range of 1 to 150 MPa was made of stainless steel with the inner diameter of 2 cm, and was connected to a pressure-gauge. Hydrostatic pressure was generated by pushing a piston into the pressure chamber through the manual control of screws. Achieving the desired amount of pressure took from 20 seconds to 5 min (10 MPa to 150 MPa, respectively); the duration of pressure release was 3 seconds. At the experiments where the effects of gradual decompression were investigated, release time was between 30-210 min. At experiments conducted at 0° C., the pressure chamber was simmered in the cooling bath of Bio-cool (FTS-Systems, NY, USA).

Cryopreservation with Previous Pressurization

Embryos were randomly allocated to three groups. Blastocysts of Group I. were cryopreserved as mentioned below, in a vitrification solution containing 7 M Ethylene glycol (EG) according to Nowshari and Brem (1998). Embryos of Group II. were treated with 60 MPa pressure for 30 min, then were frozen in the same way. Group III. served as untreated control. After thawing, embryos were cultured in vitro for 24 hours.

Cryopreservation

Embryos were equilibrated for 5 min in a solution containing 1.5 M ethylene glycol (EG) (Sigma, USA) and 0.25 M sucrose in M2 (Sigma, USA), supplemented with 10% Fetal Calf Serum (FCS) (Sigma, USA), then transferred into a vitrification solution (7 M E, 0.5 M sucrose in M2 with 10% FCS) pre-loaded in a 0.25 ml plastic straw (7-9 embryos/straw). Finally, straws were heat-sealed. After 1 min exposure to the vitrification solution, the straw was slowly immersed in liquid nitrogen. Straws were thawed by transfer into 30° C. water for 30 sec and then the embryos were recovered and placed in rehydration medium (0.5 M sucrose in M2 supplemented with 10% FCS) for 5 min. Embryos then were cultured in medium G 2.2 as described above Nowshari and Brem, 1998).

Embryo Transfer

Embryos were cultured in G 2.2 for 2 hours as above. Then, they were separated in each experimental group as 'dead' and 'survived' and were transferred separately (7-12 embryos per animal) to Day 3 pseudopregnant recipients. Untreated blastocysts were transferred as controls.

Evaluation and Statistical Analysis

Embryo quality was examined just after releasing the pressure or after thawing and after 2, 3, 4, 6, 12, 20 and 24 hours. The embryo survival was evaluated upon morphological appearance: intactness of the blastomeres re-expansion of the blastocoel, and hatching from the zona pellucida were the signs of survival. Untreated blastocysts were used as controls.

For in vivo evaluation, pressurized embryos were cultured in G 2.2 for 2 hours as above. Then 7-12 embryos per animal were transferred into Day 3 pseudopregnant recipients. Untreated blastocysts were transferred as controls. Birth of healthy pups was proof of in vivo survival of the embryos.

The survival rates were compared to control by chi-square test.

Example 1

Survival of Mouse Embryos at Different Pressures on Room Temperature

In the present experiments embryos were exposed to different hydrostatic pressures from 10 to 150 MPa (by 10 MPa increments) for various times, between 1 sec to 300 min, at room temperature.

The treatment exceeding a certain amount of pressure and time (FIG. 1) caused reversible morphological changes. The expanded blastocysts compacted inside the zona pellucida:

the blastocoel disappeared, the size of the blastomeres reduced but their structural integrity showed no alteration. After 4-5 hours of in vitro culture these blastocysts re-expanded and hatched from the zona pellucida in 24 hours (a). Embryos receiving less impact showed no morphological change and hatched within 24 hours of in vitro culture (b), while embryos challenged with a greater impact did not re-expand from the compacted stage and disintegrated within 2 hours, or were already disintegrated after decompression (c) (FIG. 1).

For in vivo evaluation, challenged embryos were judged 'survived' (a&b) and 'dead' (c) after 2 hours of in vitro culture after decompression and were transferred into recipients separately. Out of 170 transferred 'a' and 'b' embryos, 145 healthy pups were born (85%), but 0 were born from 49 'c' embryos (0%).

There were no significant differences between the hatching rate (in vitro) and birth rate (in vivo) of the non pressurized control, the compacted and the non-compacted pressurized 'a' and 'b' embryos (p<0.05).

These results show that embryos can survive a substantial amount of pressure without any change in their survival rate, though the higher the magnitude of the pressure, the less time the embryos survive (FIG. 1). Embryos that do not disintegrate within 2 hours of in vitro culture have identical in vitro and in vivo survival rates than the untreated controls.

Example 2

Survival of Mouse Embryos after Using Different Decompression Profiles

In the present experiment we investigated whether the survival rate of pressurized embryos could be improved by gradual decompression.

Expanded blastocysts were kept at 90 MPa for 30, 60 and 120 minutes, (where the survival rate at room temperature with instant decompression was 50%, 0% and 0%, respectively) then the pressure was gradually released in 9 steps for 30, 60, 90, 120 and 150 minutes. The results show that survival can be significantly improved by gradual decompression, which has an optimal range depending on the time the embryos spend under pressure. The optimal come-up time rose the longer the time embryos spent under pressure. The maximal survival rate, achievable by decompression, reduced as the time of the pressurization increased (FIG. 2).

At in vitro evaluation 54 'survived' and 35 'dead' embryos were transferred to 9 recipients. Out of 54 'survived' embryos 47 implanted (87%), but 0 embryos implanted out of the 35 'dead' embryos at the 18 days count. The implantation rate of the 'survived' group is not different from that of the controls (p<0.05).

Example 3

Survival of Mouse Embryos at Different Pressures at Low Temperature

In this experiment the role of temperature was investigated on the survival capacity of the pressurized embryos.

30, 60 and 90 MPa pressure was applied to embryos for 1 sec, 5, 10, 15, 30 and 60 min. at low temperature (0° C.). While non-pressurized embryos can live at 0° C. for a substantial amount of time without any significant change in their survival, simultaneous pressure treatment with 30, 60, 90 MPa was lethal for 100% of the embryos after 45, 10, 5 min, respectively. A significantly reduced survival rate was observed with the embryos pressurized at low temperature compared to the groups treated at room temperature (P<0.01%) (FIGS. 3a, 3b).

At in vitro evaluation 40 'survived' and 28 'dead' embryos were transferred to 7 recipients. out of the 40 'survived' embryos 34 implanted (85%), and 0 embryos implanted out of the 28 'dead' embryos at the 18 days count. The implantation rate of the 'survived' group is not different from that of the control (p<0.05).

Embryos kept at 0° C. under 90 MPa pressure for 30 minutes were also decompressed gradually. No embryos survived at any of the retrieval times we used (30 60, 90, 120, 150, 180 min). Eight to twelve embryos were used in each group, experiments were repeated for 3 times.

Example 4

Survival of Mouse Embryos after Pressure Treatment, Freezing and Thawing

In the present study we explored whether the survival rate of cryopreserved expanded mouse blastocysts could be improved by pressure treatment before the freezing procedure. Results are presented in Table 1.

TABLE 1

Survival of frozen-thawed embryos cryopreserved with/without previous pressure treatment

|  | n | Signs of survival after 6 hours | | Signs of survival after 20 hours | | | |
|---|---|---|---|---|---|---|---|
|  |  | ½ expanded | Fully expanded | ½ expanded | ⅔ expanded | Fully expanded | Hatched |
| Group I | 115 | 9% | 0%[b] | 17% | 10% | 19% | 0%[b] |
| Group II (Pressure treated) | 95 | — | 98%[a] | — | — | 3% | 95%[a] |
| Untreated Control | 107 | — | 99%[a] | — | — | 5% | 94%[a] |

Letters with different superscript are significantly different from each other (p < 0.01)

Significant differences were observed in the survival rate between the pressurized and non pressurized groups (p<0.01). The re-expansion was faster (4-6 hours vs. 20 hours) and the survival rate was higher (98% vs. 46%) in those embryos that received pressure treatment before cryopreservation (Table 1). There was no significant difference between the control and the pressure treated group in the survival and hatching rate.

Example 5

Survival of Bovine Embryos after Pressure Treatment, Freezing and Thawing

Materials and Methods

Oocyte Collection and In Vitro Maturation (IVM)

Chemicals were purchased from EMBRAPA (Brasilia, Brazil) unless otherwise indicated. Ovaries were collected from slaughter house and kept in physiological water at 35-37° C. Cumulus-oocyte complexes (COCs) were obtained by aspiration of 2-10 mm follicles using 20 ml syringe with 18 G needle and were collected into 50 ml centrifuge tubes. After 10 minutes of sedimentation COCs were aspirated into Petri dishes with TCM-199 Hank's (Gibco) supplemented with fetal calf serum (FCS), penicillin, streptomycin and heparin (Sigma H3149). After the collection COCs were washed three times in the maturation medium (TCM-199 Earl's supplemented with FCS, LH (Sigma), FSH (Sigma), L-Glutamine, penicillin and streptomycin) and were transferred into 2 ml of maturation medium (approximately 100 COCs per Petri dish), covered with mineral oil. Oocites were matured in 38° C. with 5% $CO_2$ and maximal humidity in air for 22 hours.

Sperm Preparation, In Vitro Fertilization (IVF) and In Vitro Culture (IVC)

For IVF, COCs were washed three times in fertilization medium before being transferred in groups of 20-25 into Petri dishes containing four drops of 2001 µl of fertilization medium (TALP supplemented with BSA, penicilamine—Sigma P4875, hipotaurin—Sigma H1384, epinefrin—Sigma E4250 and heparin—Sigma H3149) covered with mineral oil. Motile spermatozoa were obtained by centrifugation of frozen-thawed spermatozoa (Gentec, Cuiaba, Brazil) on a Percoll discontinuous density gradient (2 ml of 45% Percoll over 2 ml of 90% Percoll) for 20 min at 700 g at room temperature. Spermatozoa pellet, collected at the bottom of the 90% fraction, were washed in HEPES-buffered Tyrode's and pelleted by centrifugation at 700 g for 5 min. Spermatozoa were counted in a hemocytometer and diluted in the appropriate volume of TALP to give a concentration of $2 \times 10^6$ spermatozoa/ml; a 200 µl aliquot of this suspension was added to each fertilization drop. Plates were incubated for 19 hr in 5% $CO_2$ in humidified air at 39° C. Presumptive zygotes were then cultured in vitro in SOF droplets under mineral oil in a humidified atmosphere of 5% CO at 39° C.

Pressurization

Expanded blastocysts were loaded into 0.25 ml plastic straws without air-bubbles (7-9 embryos/straw), with embryo holding medium (Emcare Holding, Emcare, New Zealand), then straws were sealed with PVC. Straws were placed into the pressurechamber filled with water as pressure medium. Embryos were exposed to different hydrostatic pressures from 60 to 90 MPa (by 10 MPa increments) for various times (15, 30, 45, 50, 60, 90, 100 minutes), at room temperature, as detailed above.

Cryopreservation with Previous Pressurization

Embryos were randomly allocated to three groups. Blastocysts of Group I were cryopreserved as mentioned below, in a freezing solution containing 1.5 M Ethylene glycol (EG). Embryos of Group II were treated with 80 MPa pressure for 50 min, then were frozen in the same way. The time interval between the beginning of the freezing and the pressure treatment was between 4 to 5 minutes. Group III served as untreated control. After thawing, embryos were cultured in vitro for 24 hours.

Cryopreservation

Blastocysts were equilibrated for 8 minutes in freezing solution consisting of 1.5 M ethylene glycol (Emcare, New Zealand) pre-loaded in a 0.25 ml plastic straw (7-9 embryos/straw). Straws were sealed with PVC. Straws were placed into a programmable freezer (Bio-cool, FTS-Systems, USA, NY) precooled to −5.2° C. After 3 min, seeding was induced. Following a further 10 min, straws were cooled at −0.5° C./min to −32° C., following which they were plunged into liquid nitrogen. Straws were thawed by 10 sec gentle agitation in air followed by placing the straw into 35° C. water until the ice in the straw melted. Blastocysts were recovered from the straws, washed three times in SOF and were moved to SOF under mineral oil and returned to the incubator for 24 hr.

Evaluation and Statistical Analysis

Embryo quality was examined just after releasing the pressure or after thawing and after 2, 3, 4, 6, 12, and 24 hours. The embryo survival was evaluated upon morphological appearance and continued in vitro development: intactness of the blastocysts, re-expansion of the blastocoel, and hatching from the zona pellucida were the signs of survival. Untreated blastocysts were used as controls.

The survival rates were compared to control by chi-square test. The probability value of P<0.05 was taken as statistically significant.

Results

Survival and Continued Development of Embryos after Various Pressure Treatments

In the first set of experiments embryos were exposed to different hydrostatic pressures for various times. Results are summarized in Table 2 below:

TABLE 2

Survival of frozen-thawed bovine embryos cryopreserved with/without previous pressure treatment

| Pressure | Time | n (compacted after decompression/non~) | continued development 6 h | | continued development 24 h (hatched) | |
|---|---|---|---|---|---|---|
| | | | I-II | III-IV | I-II | III-IV |
| 80 MPa | 45 min | 8 (5/3) | 8 | — | 8 (4) | — |
| 60 MPa | 60 min | 8 (3/5) | 8 | — | 8 (5) | — |
| 90 MPa | 45 min | 7 (7/0) | 4 | 3 | 4 (1) | 3 |
| 90 MPa | 30 min | 7 (3/4) | 6 | 1 | 6 (6) | 1 |
| control | | 8 | 7 | 1 | 6 (2) | 2 |

I-II: fully or ⅔ re-expanded first or second class embryos;
III-IV: third class or dead embryos Continued In Vitro Development of Blastocysts Vitrified with and without Pressure Pre-Treatment In the second study we explored whether the continued in vitro development of cryopreserved expanded in vitro matured/fertilized/cultured bovine blastocysts could be improved by pressure treatment before the freezing procedure. 8-12 embryos were used in each experimental group, experiments were repeated 6 times. Results are presented in Table 3.

Significant differences were observed in the in vitro survival rate between the pressurized and non pressurized groups (p<0.01). The re-expansion was faster (1-2 hours vs. 4-6 hours) and the survival rate was higher (81% vs. 41%) in those embryos that received pressure treatment before cryopreservation (Table 3). There was no significant difference between the control and the pressure treated group in the survival and hatching rate.

TABLE 3

In vitro continued development of IVMFC bovine blastocysts after thawing, frozen with or without pressure pre-treatment

| | | 1 h | | 4 h | | | 12 h | | | 24 h | |
|---|---|---|---|---|---|---|---|---|---|---|---|
| | n | I + II | IV | I + II | IV | Hatched | I + II | IV | Hatched | I + II | IV |
| Frozen with pre-treatment | 59 | 88% | 12% | 81% | 19% | 12% | 81% | 19% | 17% | 81% | 19% |
| Non treated | 61 | 46% | 54% | 41% | 59% | 0% | 41% | 59% | 0% | 41% | 59% |

I-II: fully or ⅔ re-expanded first or second class embryos;
IV: dead embryos

Conclusions

Our results showed that the applied pressure treatment prior to freezing could improve the in vitro developmental speed, survival and hatching rates of the IVMFC (in vitro maturation of the oocytes, in vitro fertilization, in vitro culture of embryos) bovine embryos. This study provides further evidence that a pressure impulse can greatly add to the success of cryopreservation. It is appreciated that the methods presented in the above experiments are easily adaptable to a whole range of biological material, in particular embryos of different origin, for example equine, caprine, swine or primate, including human embryos.

Example 6

Survival of Sperm after Pressure Treatment, Freezing and Thawing

In the first part of the present study we intended to describe how HHP affects the ratio of the motile cells of the fresh bull semen. In the second part of the experiment we have chosen 4 parameter-pairs from the pressure-time-sperm motility chart drawn up, and compared the post-thaw motility of the frozen bull-semen pre-treated with the chosen pressure-time parameters with the ones that were frozen without pre-treatment.

Samples of semen were obtained at the Artificial Insemination Centre of Klessheim, Austria. Sample was diluted to a sperm concentration of $8 \times 10^7$/ml with AndroMed extender (MiniTub, Germany) as described in the prescription. The diluted sperm was loaded into 0.25 ml straws and kept at room temperature. Before the pressure treatment the straw with the semen sample was cut into two parts. One half was heat sealed and then pressurized with a specific pressure/time parameter, the other half was used to compare the post-pressure motility. Experiments at each pressure/time parameters were repeated for seven times, progressive motility was assessed individually by light microscopic investigation by two separate assistants. The treatment groups were challenged with the following parameters: 10 MPa for 30, 60, 90 and 120 min; 30 MPa for 30, 60, 90, 120 and 510 min; 50 MPa for 30, 60 and 90 min; 70 MPa for 30, 60 and 90 min; 90 MPa for 30, 60, 90, 120 and 510 min. The pressurizing device was custom made of stainless steel, comprising a pressure chamber with water as a pressure medium, and an authority-approved pressure gauge. The time of reaching the desired amount of pressure was between one to five minutes, depressurization took between two to three seconds.

The average motility of the control samples ranged between 75 to 90 percent, while the average motility of the pressurized samples ranged between 55 (90 MPa/120 min) to 84 (10 MPa/30 min) percent. The groups of 30 MPa/510 min and 90 MPa/510 min had significantly reduced motility compared to the other pressurized groups (27% and 33%, respectively; p<0.05). See FIG. 4.

In the second part of the trial samples of semen were obtained from two bulls (one with a history of very poor freezability). Samples were diluted as above, than were divided into four treatment groups. The treatment groups were split: one half was heat sealed and pressurized with I: 90 MPa/30 min; II: 90 MPa/90 min; III: 30 MPa/30 min; IV: 30 MPa/90 min prior to freezing, the other half was frozen without pre-treatment with the same freezing protocol (60 min equilibration at 5° C., then 10 minutes at −110° C. before plunging into liquid nitrogen). Thawing was performed in 35° C. water-bath for 30 seconds. Each group was also tested for initial motility with and without pressurization. Each trial was repeated for eight times.

The average initial motility of both of the bulls was between 65 and 80 percent, while after pressurization it has reduced to between 45 to 75 percent. The average post thaw motility of both of the bulls was significantly superior with pressure pretreatment compared to the samples frozen without previous pressurization (p<0.001) (Bull I: 2-3% without pressurization vs. 17-33% with pressurization—FIG. 5; Bull II:

0% without pressurization vs. 21-35% with pressure pretreatment—FIG. 6). Amongst the parameters used, 30 MPa/90 min proved significantly superior (33 and 35%; p<0.05).

The present study clearly describes the beneficial effect of a previous pressure treatment to the post thaw motility of bull semen cryopreserved in our experiment. This study provides further evidence that a pressure impulse can greatly add to the success of cryopreservation. It is appreciated that the methods presented in the above experiments are easily adaptable to a whole range of biological material, in particular sperms of different origin, for example equine, caprine, swine or primate, including human origin.

INDUSTRIAL APPLICABILITY

The results presented in the above examples show that the pressure treatment applied prior to cryopreservation obviously improves the in vitro developmental speed, survival and hatching rates of the embryos. Consequently, the ultimate goal of all such effort can be achieved: generation of more offspring. Also, the presented data on bovine embryos and bull sperm indicates the wide applicability of the inventive concept for cryopreserving biological materials. The application of the method according to the present invention can be useful in improving success rates in all kind of embryo-cryopreservation and embryo-manipulation, including other mammalian species, humans not excluded, as well as application for oocytes, embryonic stem cells, tissues and the like. The present method also opens wide possibilities for other fields where cryopreservation of biological material can find its applications.

REFERENCES

Abe, F., and Horikoshi, K. (1995). Hydrostatic pressure promotes the acidification of vacuoles in *Saccharomyces cerevisiae*. FEMS Microbiol Lett 130, 307-312.

Abe, F., and Horikoshi, K. (1997). Vacuolar acidification in *Saccharomyces cerevisiae* induced by elevated hydrostatic pressure is transient and is mediated by vacuolar H+-ATPase. Extremophiles 1, 89-93.

Abe, F., and Horikoshi, K. (1998). Analysis of intracellular pH in the yeast Saccharomyces cerevisiae under elevated hydrostatic pressure: a study in baro- (piezo-) physiology. Extremophiles 2, 223-228.

Abe, F., Kato, C., and Horikoshi, K. (1999). Pressure-regulated metabolism in microorganisms. Trends Microbiol 7, 447-453.

Aldridge, B. E., Bruner, L. J. (1985). Pressure effects on mechanisms of charge transport across bilayer membranes. Biochim Biophys Acta 817, 343-354.

Archer, J., Gook, D. A., Edgar, D. H. (2003). Blastocyst formation and cell numbers in human frozen-thawed embryos following extended culture. Human Reproduction (Oxford, England) 18, 1669-1673.

Baguisi, A., Arav, A., Crosby, T. F., Roche, J. F., and Boland, M. P. (1987). Hypothermic storage of sheep embryos with antifreeze proteins: development in vitro and in vivo. Theriogenology 48, 1017-1024.

Bridgman, P. W. (1911). Water in the liquid and five solid forms under pressure. Proceedings of the American Academy of Arts and Science 47, 441-558.

Bridgeman, P. E. (1970). The physics of high pressure. New York:Dover

Butz P, Ludwig H. (1986). Pressure inactivation of microorganisms at moderate temperatures. Physica B+C 139-140, 875-877.

Fahy, G. M., MacFarane, D. R., Angell, C. A. and Meryman, H. T. (1984). Vitrification as an approach to cryopreservation. Cryobiology 21. 407426.

Fukuda, A., Osawa, T., Oda, H., Tanaka, T., Toyokuni, S. and Uchida, K. Oxidative stress response in iron induced acute nephrotoxicity: enhanced expression of heat shock protein 90. Biochem Biophys Res Commun 1996; 219:76-81.

Garcia-Gardena, G., Fan, R., Shah, V., Sorrentino, R., Cirino, G., Papapetropoulos.

Dynamic activation of endothelialnitric oxide synthase by HSP90. Nature 1998; 392: 821-4.

Graumann, P. L., Marahiel M. A. (1999). Cold shock proteins CspB and CspC are major stationary-phase-induced proteins in *Bacillus subtilis*. Arch Microbiol 171, 135-138.

Gross, M., Jaenicke, R. (1994). Proteins under pressure. The influence of high hydrostatic pressure on structure, function and assembly of proteins and protein complexes. Eur J Biochem 221, 617-630.

Huang, S. Y., Kuo, Y. H., Lee, W. C., Tsou, H. L., Lee, Y. P., Chang, H. L. et al. Substantial decrease of heat-shock protein 90 precedes the decline of sperm motility during cooling of boar spermatozoa. Theriogenology 1999; 51:1007-16.

Huang, S. Y., Kuo, Y. H., Tsou, H. L., Lee, W. C., King, Y. T., Huang, H. C. et al. The decline of porcine sperm motility by geldanamycin, a specific inhibitor of heat shock protein 90 (HSP90). Theriogenology 2000; 53:1117-84.

Ishwar, A. K., Memon, M. A. (1996). Embryo transfer in sheep and goats: a review. Small Ruminant Research 19, 3543.

Jaenicke, R. (1991). Protein stability and molecular adaptation to extreme conditions. Eur J Biochem 202, 715-728.

LaTena, A., Brandi, A., Falconi, M., Spurio, R., Pon, C. L., Gualerzi, C. O. (1991). Identification of a cold-shock transcriptional enhancer of the *Escherichia coli* major cold shock gene encoding nucleotide protein H—NS. Proc Natl Acad Sci USA 88, 10907-10911.

Leibo, S. P. and Songsasen, N. (2002). Cryopreservation of gamets and embryos of non-domestic species. Theriogenology 57. 303-326.

Macdonald, A. G. (1987). The role of membrane fluidity in complex processes under high pressure. In: Jonnasch, H. W., Marquis, R. E., Zimmerman, A. M., editors. Current Perspectives in High Pressure Biology. London: Academic Press pp. 207-223.

Medeiro, C. M. O., Forell, F., Oliveira, A. T. D., and Rodrigues, 2002. J. L. Current Status Of Sperm Cryopreservation: Why Isn't It Better? Theriogenology 57:327-344.

Murakami, T. H., Zimmerman, A. M. (1973). DNA synthesis in Tetrahymena: a pressure study. Cytobios 7, 171-181.

Nowshari, M. A., Brem, G. (1998). Effect of cryoprotectants and their concentration on post-thaw survival and development of expanded mouse blastocysts frozen by a simple rapid-freezing procedure. Theriogenology 50, 1001-1013.

Palou, E., Lopez-Malo, A., Barbosa-Canovas, G. V., Welti-Chanes, J., and Swanson, B. G. (1997). Kinetic analysis of *Zygosaccharomyces* bailii inactivation by high hydrostatic pressure. Lebensm.-Wiss.U.Technol. 30, 703-708.

Pearl, L. H. and Prodromou, C. Structure and in vivo function of Hsp 90. Curr. Opin Struct Biol 2000; 10:46-51.

Péqueux, A., and Gilles, R. (1978). Effects of high hydrostatic pressures on the activity of the membrane ATPases of some organs implicated in hydromineral regulation. Comp Biochem Physiol B Biochem Mol Biol 59, 207-212.

Phadtare, S., Alasina, J., Inouye, M. (1999). Cold-shock response and cold-shock proteins. Curr Opin Microbiol 2, 175-180.

Phadtare S., Alasina J. and Inouye M. (1999). Cold-shock response and cold-shock proteins. Curr Opin Microbiol 2, 175-180 Graumann, P. L. and Marahiel, M. A. (1999). Cold shock proteins CspB and CspC are major stationary-phase-induced proteins in *Bacillus subtilis*. Arch Microbiol 171. 135-138.

Prodromou, C., Roe, S. M., O'Brian, R., Ladbury, J. E., Piper, P. W. and Pearl, L. H. Identification and structural characterization of the ATP/ADP-binding site in the HSP90 molecular chaperone. Cell 1997; 90:65-75.

Rall, W. F., and Fahy, G. M. (1985). Ice-free cryopreservation of mouse embryos at −196° C. by vitrification. Nature 313, 573-575.

Reubinoff, B. E., Pera, M. F., Vajta, G., and Trounson, A. O. (2001). Effective cryopreservation of human embryonic stem cells by the open pulled straw vitrification method. Human Reproduction 16, 2187-2194.

Routray, P., Suzuki, T., Strüssmann, C. A. and Takai, R. (2002). Factors affecting the uptake of DMSO by the eggs and embryos of medaka, *Oryzias latipes*. Theriogenology 58. 1483-1496.

Schmid, G., Lüidemann, H. D., and Jaenicke, R. (1975) High pressure effects on the activity of glycolytic enzymes. Biophys Chem 3, 90-98.

Schuster, B., Sleytr, U. B. (2002). The effect of hydrostatic pressure on Slayer-supported lipid membranes. Biochim Biophys Acta 1563, 29-34.

Seki, K., Toyoshima, M. (1998). Preserving tardigrades under pressure. Nature 395, 853-854.

Silva, J. L., Foguel, D., Royer, C. A. (2001). Pressure provides new insights into protein folding, dynamics and structure. Trends Biochem Sci 26, 612-618.

Spilimbergo, S., Elvassore, N., Bertucco, A. (2002). Microbial inactivation by high-pressure. The Journal of Supercritical Fluids 22, 55-63.

Stachecki, J, J., Cohen, J., Schimmel, T., Willadsen, S. M. (2002). Fetal development of mouse oocytes and zygotes cryopreserved in a nonconventional freezing medium. Cryobiology 44, 5-13.

Van Wagtendonk-De Leeuw, A. M., Den Daas, J. H., Kruip, T. A., Rall, W. F. (1995). Comparison of the efficacy of conventional slow freezing and rapid cryopreservation methods for bovine embryos. Cryobiology 32, 157-167.

Van Wagtendonk-De Leeuw, A. M., Den Haas, J. H. G., and Rall, W. F. 1997. Field trials to compare pregnancy rates of bovine embryo cryopreservation methods: vitrification and one-step dilution versus slow freezing and three-step dilution. Theriogenology 48, 1071-1084.

Watson, P. F. The effect of cold shock on sperm cell membranes. In: Morris, G. J. and Clarke, A. eds. Effects of low temperature on biological membranes. London: Academic Press; 1981. p. 189-218.

Weber, G., Drickamer, H. G. (1983). The effect of high pressure upon proteins and other biomolecules. Q Rev Biophys 16, 89-112.

Welch, T. J., Farewell, A., Neidhardt, F. C., Bartlett, D. H. (1993). Stress response of *Escherichia coli* to elevated hydrostatic pressure. J Bacteriol 175, 7170-7177.

Wemekamp-Kamphuis, H. H., Karatzas, A. K., Wouters, J. A., Abee, T. (2002). Enhanced levels of cold shock proteins in *Listeria monocytogenes* L028 upon exposure to low temperature and high hydrostatic pressure. Appl Environ Microbiol 68, 456-63.

Wen-Lei, C., Yi-Xin, W., Zu-Qiong, X. and Zheng, L. (2003). Cryopreservation—induced decrease in heat-shock protein 90 in human spermatozoa and its mechanism. Asian Journal Of Andrology 5. 43-46.

Wouters, J. A., Jeynov, B., Rombouts, F. M., de Vos, W. M., Kuipers, O. P., Abee, T. (1999). Analysis of the role of 7 kDa cold-shock proteins of *Lactobacillus* lactis MG1363 in cryoprotection. Microbiology 145, 3185-3194.

Yager, P., Chang, E. L. (1983). Destabilization of a lipid non-bilayer phase by high pressure. Biochim Biophys Acta 731, 491-494.

Yamanaka, K., Fang, L., Inouye, M. (1998). The CspA family in *Escherichia coli*: multiple gene duplication for stress adaptation. Mol Microbiol 27, 247-255.

The invention claimed is:

1. A method for improving post-thaw survival of cryopreserved viable biological material comprising:
   (a) applying hydrostatic pressure in the range of 10 to 200 MPa to said viable biological material, optionally according to a predetermined pressure-time profile;
   (b) keeping the said biological material at the hydrostatic pressure for a predetermined time period;
   (c) releasing the hydrostatic pressure;
   (d) further cryopreserving the said viable biological material using any protocol applicable thereto,
   wherein the viable biological material is mammalian blastocyst or mammalian sperm.

2. The method according to claim 1 wherein the said hydrostatic pressure is applied for a time period between 1 second and 300 minutes.

3. The method according to claim 2 wherein the said hydrostatic pressure is applied for a time period between 1 second and 150 minutes.

4. The method according to claim 2 wherein the said hydrostatic pressure is applied for a time period between 1 second and 90 minutes.

5. The method according to claim 2 wherein the said hydrostatic pressure is applied for a time period between 1 second and 60 minutes.

6. The method according to claim 1 wherein the pressure is released gradually over a time period between 1 second and 4 hours.

7. The method according to claim 1, further comprising before step (a), placing the biological material into a pressurizing device.

8. The method according to claim 7, wherein a control system is provided for controlling the depressurization of the pressure chamber over a time period between 1 second and 4 hours.

9. The method according to claim 7, wherein the pressurizing device includes a pressure chamber suitable for receiving the biological material, and means to provide controlled pressure in the range of 1 to 200 MPa.

10. The method according to claim 9 wherein said means provides controlled pressure in the range of 10 to 100 MPa.

11. The method according to claim 9 wherein said means provides controlled pressure in the range of 20 to 75 MPa.

12. The method according to claim 9 wherein said means provides controlled pressure in the range of 30 to 60 MPa.

13. The method according to claim 9, wherein the pressurizing device comprises means to maintain the said pressure for a time period between 1 second and 300 minutes.

14. The method according to claim 13, wherein said pressure is maintained for a time period between 1 second and 150 minutes.

15. The method according to claim 13, wherein said pressure is maintained between 1 second and 60 minutes.

16. The method according to claim 1 wherein the said hydrostatic pressure is in the range of 10 to 100 MPa.

17. The method according to claim 1, wherein the said hydrostatic pressure is in the range of 20 to 75 MPa.

18. The method according to claim 1 wherein the said hydrostatic pressure is in the range of 30 to 60 MPa.

* * * * *